US012140916B2

(12) United States Patent
Katz et al.

(10) Patent No.: US 12,140,916 B2
(45) Date of Patent: Nov. 12, 2024

(54) WEARABLE COMPUTER POINTING APPARATUS

(71) Applicant: 6Degrees Ltd., Tel-Aviv (IL)

(72) Inventors: Aryeh Haim Katz, Safed (IL); Miri Berger Katz, Ramat Gan (IL)

(73) Assignee: 6DEGREES LTD., Tel-Aviv (IL)

( * ) Notice: Subject to any disclaimer, the term of this patent is extended or adjusted under 35 U.S.C. 154(b) by 0 days.

(21) Appl. No.: 18/319,150

(22) Filed: May 17, 2023

(65) Prior Publication Data

US 2024/0126226 A1    Apr. 18, 2024

Related U.S. Application Data

(63) Continuation of application No. 14/426,131, filed as application No. PCT/IB2012/056081 on Nov. 1, 2012, now Pat. No. 11,662,699.

(51) Int. Cl.
*G05B 15/02* (2006.01)
*A61B 5/103* (2006.01)
(Continued)

(52) U.S. Cl.
CPC ............ *G05B 15/02* (2013.01); *A61B 5/103* (2013.01); *G06F 3/011* (2013.01); *G06F 3/0346* (2013.01); *A61B 5/11* (2013.01)

(58) Field of Classification Search
CPC ... A61B 5/6828; A61B 5/1107; A61B 5/1122; A61B 5/6824; A61B 5/7285;
(Continued)

(56) References Cited

U.S. PATENT DOCUMENTS 6,413,190 B1    7/2002    Wood et al.
6,965,842 B2    11/2005    Rekimoto
(Continued)

FOREIGN PATENT DOCUMENTS

CN    102247151 A    11/2011
EP    2915163 A1    9/2015
(Continued)

OTHER PUBLICATIONS

"User control of lower limb prosthetics", University of Iceland, Leturprent, Reykjavik, Iceland, Jan. 2010; Retrieved from the Internet: <URL: hllp://skemman.is/stream/gel/1946/4396/12811/2/SGK_MSc_Thesis_fixed.pdf> Karlsson S. G. Jan. 31, 2010(Jan. 31, 2010).

(Continued)

*Primary Examiner* — Christopher E Leiby
(74) *Attorney, Agent, or Firm* — Goodwin Procter LLP

(57) ABSTRACT

An upper-arm computer pointing apparatus, comprising: at least one orientation measurer, deployable on at least one area of an upper arm of a user, configured to measure orientation of the upper arm, at least one pressure meter, deployable on at least one area of the upper arm, configured to measure pressure applied by muscle of the upper arm, a computer processor, associated with the orientation measurer and pressure meter, configured to derive control data from the measured orientation and pressure, and a data transmitter, associated with the computer processor, configured to transmit the control data to a computing device.

20 Claims, 7 Drawing Sheets

(51) Int. Cl.
*G06F 3/01* (2006.01)
*G06F 3/0346* (2013.01)
*A61B 5/11* (2006.01)

(58) Field of Classification Search
CPC ... A61B 5/7278; A61B 5/6887; A61B 5/1128;
A61B 5/1118; A61B 5/1114; A61B
5/1112; A61B 5/0077; A61B 5/0004;
A61B 5/0022; A61B 2562/0247; A61B
2503/10; G16H 40/67; G16H 20/30;
G16H 10/60; G06F 3/017; G06F 3/011;
G06F 3/015; G06F 19/3418; G06F 1/163;
A63B 24/0062; A63B 24/0006; A63B
2220/836; A63B 2220/806; A63B
2220/62; A63B 2220/56; A63B 2220/12;
A63B 2220/808; A63B 2208/03; A63B
2225/50; A63B 2225/20
See application file for complete search history.

(56) References Cited

U.S. PATENT DOCUMENTS

| | | | |
|---|---|---|---|
| 7,602,301 B1 | | 10/2009 | Stirling et al. |
| 7,970,586 B1* | | 6/2011 | Kahn ................ A63F 13/45 |
| | | | 709/236 |
| 8,170,656 B2 | | 5/2012 | Tan et al. |
| 8,172,722 B2 | | 5/2012 | Molyneux et al. |
| 8,593,286 B2 | | 11/2013 | Razoumov et al. |
| 8,818,478 B2 | | 8/2014 | Scheffler et al. |
| 2005/0250994 A1 | | 11/2005 | Krullaards |
| 2006/0036141 A1* | | 2/2006 | Kamath ............... A61B 5/0031 |
| | | | 600/345 |
| 2006/0079801 A1 | | 4/2006 | DeLuca et al. |
| 2009/0153477 A1 | | 6/2009 | Saenz |
| 2009/0196460 A1 | | 8/2009 | Jakobs et al. |
| 2009/0221943 A1* | | 9/2009 | Burbank ............... A61H 1/0266 |
| | | | 601/46 |
| 2009/0326406 A1 | | 12/2009 | Tan et al. |
| 2009/0327171 A1 | | 12/2009 | Tan et al. |
| 2010/0022354 A1 | | 1/2010 | Fisher |
| 2010/0137735 A1 | | 6/2010 | Hoppe |
| 2010/0259472 A1 | | 10/2010 | Radivojevic et al. |
| 2010/0302137 A1 | | 12/2010 | Benko et al. |
| 2011/0054782 A1 | | 3/2011 | Kaahui |
| 2011/0074680 A1 | | 3/2011 | Moore |
| 2011/0132181 A1 | | 6/2011 | Kockovic |
| 2011/0148755 A1 | | 6/2011 | Lee et al. |
| 2011/0199296 A1 | | 8/2011 | Simpson |
| 2011/0199303 A1 | | 8/2011 | Simpson |
| 2011/0199393 A1 | | 8/2011 | Nurse et al. |
| 2011/0264238 A1* | | 10/2011 | van der Merwe ........ A61F 2/54 |
| | | | 623/24 |
| 2012/0046901 A1 | | 2/2012 | Green et al. |
| 2012/0053440 A1 | | 3/2012 | Chardon et al. |
| 2012/0075173 A1 | | 3/2012 | Ashbrook et al. |
| 2012/0127070 A1 | | 5/2012 | Ryoo et al. |
| 2012/0139731 A1* | | 6/2012 | Razoumov ........... A61B 5/0022 |
| | | | 340/573.1 |
| 2012/0144981 A1 | | 6/2012 | Ciccone |
| 2012/0157886 A1 | | 6/2012 | Tenn et al. |
| 2012/0188083 A1 | | 7/2012 | Miller, II |
| 2012/0256833 A1 | | 10/2012 | Chiang |
| 2012/0259648 A1 | | 10/2012 | Mallon et al. |
| 2012/0266358 A1 | | 10/2012 | Yuen |
| 2012/0316456 A1 | | 12/2012 | Rahman et al. |
| 2013/0050126 A1 | | 2/2013 | Kimura et al. |
| 2013/0171599 A1 | | 7/2013 | Bleich et al. |
| 2013/0197681 A1 | | 8/2013 | Alberth, Jr. et al. |
| 2013/0245388 A1 | | 9/2013 | Rafferty et al. |
| 2014/0049465 A1* | | 2/2014 | Tremaine ............... G16H 40/63 |
| | | | 345/156 |
| 2014/0070957 A1 | | 3/2014 | Longinotti-Buitoni et al. |
| 2015/0196802 A1 | | 7/2015 | Siegel |
| 2015/0234367 A1 | | 8/2015 | Katz et al. |
| 2015/0272500 A1* | | 10/2015 | Kan-tor ................ A61B 5/7267 |
| | | | 600/300 |
| 2016/0187977 A1 | | 6/2016 | Cruz-Hernandez et al. |
| 2016/0220808 A1 | | 8/2016 | Hyde et al. |
| 2016/0256082 A1 | | 9/2016 | Ely et al. |
| 2016/0338621 A1 | | 11/2016 | Kanchan et al. |
| 2017/0082433 A1 | | 3/2017 | Huo et al. |
| 2017/0164876 A1 | | 6/2017 | Hyde et al. |
| 2017/0273746 A1 | | 9/2017 | Flexman et al. |
| 2017/0280397 A1 | | 9/2017 | Da Costa et al. |
| 2018/0249908 A1 | | 9/2018 | Anthony et al. |

FOREIGN PATENT DOCUMENTS

| | | |
|---|---|---|
| KR | 20110070331 A | 6/2011 |
| WO | WO-2014068371 A1 | 5/2014 |

OTHER PUBLICATIONS

A Final Rejection for Korean Application No. 10-2015-7005413, Sep. 25, 2019, KIPO, Korea.

Examination Report No. 1 for Australian Patent Application No. 2017235951 dated Oct. 23, 2018, Australian Government, Red Hill, Australia.

Examiner Requisition and Examination Search Report for Canadian Patent Application No. 2,883,520 dated March 6, J019, Gatineau, QC, CIPO.

Foreign Office Action for EP Patent Application No. 19169927.1, May 11, 2020, EPO, Munich, Germany.

International Search Report issued in PCT/IB2012/056081 on Feb. 10, 2013 (2 pages).

Notice of Acceptance issued by the Australian Patent Office on Australian Patent Application No. 20122393913 dated Jun. 28, 2017.

Notification of Reason for Refusal for Korean Application No. 10-2015-7005413, Jan. 30, 2019, KIPO, Korea.

Singhal, "Muscle Controlled 3D Mouse for Amputees", 2010 Tech Briefs 2010 Contest, Jun. 30, 2010, Link: https://contesl.techbriefs.com/2010/entries/medical/1067. Singhal, "Muscle Controlled 3D Mouse for Amputees", 2010 Tech Briefs 2010 Contest, Jun. 30, 2010, Link: https://contesl.techbriefs.com/2010/entries/medical/1067.

The European Search Report for European Application No. 19169927.1 dated May 29, 2019, EPO, Munich, Germany.

X. Chen, X. Zhang, Z. Y. Zhao, J. H. Yang, V. Lantz and K. Q. Wang, "Hand Gesture Recognition Research Based on Surface EMG Sensors and 2D-accelerometers," 2007 11th IEEE International Symposium on Wearable Computers, Boston, MA, 2007, pp. 11-14. doi:10.1109/ISWC.2007.4373769ieeexplore.ieee.org/stamp/stamp.jsp?tp=&arnumber=4373769&isnumber=4373754.

* cited by examiner

WEARABLE COMPUTER POINTING APPARATUS

CROSS-REFERENCE TO RELATED APPLICATIONS

This application is a continuation of U.S. application Ser. No. 14/426,131, filed on Mar. 4, 2015, and entitled "UPPER-ARM COMPUTER POINTING APPARATUS," which is a National Stage entry of International Application No. PCT/IB2012/056081, filed on Nov. 1, 2012, entitled "UPPER-ARM COMPUTER POINTING APPARATUS," which designated the United States, each of which is hereby incorporated by reference herein in its entirety.

FIELD AND BACKGROUND OF THE INVENTION

The present invention relates to computer pointing devices and, more particularly, but not exclusively to a computer mouse wearable on the upper arm of a computer user.

The most commonly used computer pointing device is the computer mouse.

Movement of the mouse about a flat surface typically located on a desktop causes movement of the cursor about the display screen. Selection of objects is accomplished by simultaneously holding the position of the cursor on top of the object while clicking, clicking and holding, or double clicking one or more buttons located on the mouse.

For example, mouse manipulation requires the user to: grasp the mouse; move the arm and wrist to position the mouse, as needed, to perform a scrolling function or to activate the buttons.

A mouse typically has anywhere from one to three buttons and most commonly has two buttons.

A variety of conditions, such as cerebral palsy, Parkinson's disease, multiple sclerosis, arthritis, etc., can fully or partially deprive a person of the manual motor control capacities needed to use a mouse, to move a cursor to a specific location on a display screen, and/or to select objects by operation of a mouse button.

Similarly, trauma, malignancy, congenital absence, and other conditions may result in loss of fingers, wrist, forearm, etc. Consequently, a person may be deprived of manual motor control capacities needed to use a computer mouse by moving the mouse about a flat surface and/or clicking the mouse buttons.

SUMMARY OF THE INVENTION

According to one aspect of the present invention, there is provided an upper-arm computer pointing apparatus, comprising: at least one orientation measurer, deployable on at least one area of an upper arm of a user, configured to measure orientation of the upper arm, at least one pressure meter, deployable on at least one area of the upper arm, configured to measure pressure applied by muscle of the upper arm, a computer processor, associated with the orientation measurer and pressure meter, configured to derive control data from the measured orientation and pressure, and a data transmitter, associated with the computer processor, configured to transmit the control data to a computing device.

According to a second aspect of the present invention, there is provided an upper-arm computer pointing apparatus, comprising: at least one orientation measurer, deployable on at least one area of an upper arm of a user, configured to measure orientation of the upper arm, a computer processor, associated with the orientation measurer, configured to derive control data from the measured orientation, and a data transmitter, associated with the computer processor, configured to transmit the control data to a computing device.

According to a third aspect of the present invention, there is provided an upper-arm computer pointing apparatus, comprising: at least one pressure meter, deployable on at least one area of the upper arm, configured to measure pressure applied by muscle of the upper arm, a computer processor, associated with the pressure meter, configured to derive control data from the measured pressure, and a data transmitter, associated with the computer processor, configured to transmit the control data to a computing device.

According to a fourth aspect of the present invention, there is provided a method for upper-arm computer pointing, comprising: measuring orientation of an upper arm of a user, on at least one area of the upper arm, measuring pressure applied by muscle of the upper arm, on at least one area of the upper arm, deriving control data from the measured orientation and pressure, and transmitting the control data to a computing device.

According to a fifth aspect of the present invention, there is provided a method for upper-arm computer pointing, comprising: measuring orientation of the upper arm, on at least one area of the upper arm, deriving control data from the measured orientation, and transmitting the control data to a computing device.

According to a sixth aspect of the present invention, there is provided a method for upper-arm computer pointing, comprising: measuring pressure applied by muscle of the upper arm, on at least one area of the upper arm, deriving control data from the measured pressure, and transmitting the control data to a computing device.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice. In the Drawings.

DESCRIPTION OF THE PREFERRED EMBODIMENTS

Figure 1:
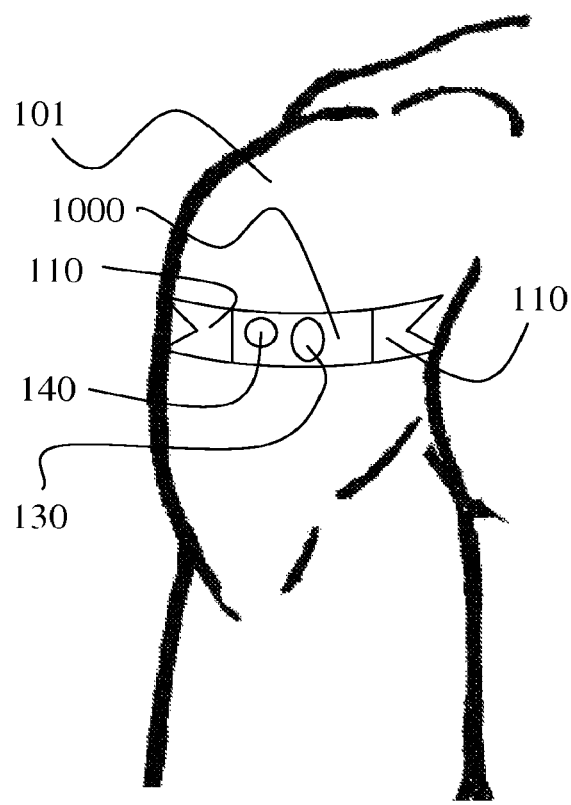
FIG. 1 is a block diagram schematically illustrating a first apparatus for upper-arm computer pointing, according to an exemplary embodiment of the present invention.

The present embodiments comprise apparatuses and methods for upper-arm computer pointing.

Currently, the most commonly used computer pointing device is the computer mouse.

Movement of the mouse about a flat surface typically located on a desktop causes movement of the cursor about the display screen. Selection of objects is accomplished by simultaneously holding the position of the cursor on top of the object while clicking, clicking and holding, or double clicking one or more buttons located on the mouse, etc.

A variety of conditions, such as cerebral palsy, Parkinson's disease, multiple sclerosis, arthritis, can fully or partially deprive a person of the manual motor control capacities needed to use a mouse, to move a cursor to a specific location on a display screen, and/or to select objects by operation of a mouse button.

In many cases, an upper extremity is amputated because of trauma from war injury, automobile accident, recreation or work-related injury. Malignancy, congenital absence of an extremity and other conditions account for a minority of amputation cases. In some countries, various levels of amputation are the result of punishment, torture and terrorism-related trauma.

An amputated person experiences loss of fingers, wrist, forearm, or other body extremity.

Consequently, the amputated person is deprived of manual motor control capacities needed to use a computer mouse by moving the mouse about a flat surface and/or clicking the mouse buttons.

An apparatus according to an exemplary embodiment of the present invention may be worn on an upper arm of a user of a computing device (such as a desktop computer or a smart cellular phone), say as a strap-on device.

The apparatus may include one or more pressure meters deployed on the upper arm, for measuring pressure applied on sides of the upper arm by muscle of the upper arm, as described in further detail hereinbelow.

The upper arm is the region between the shoulder and the elbow, composed of the humerus bone with the elbow joint at its distal end. The elbow joint is the synovial hinge joint between the humerus bone in the upper arm and the radius and ulna bones in the forearm.

Elbow extension primarily results from contraction of the triceps, a large muscle located at the posterior (back) aspect of the upper arm. The triceps muscle usually remains intact following amputation performed below the shoulder.

The apparatus may further include one or more orientation measurers (say gyroscopic devices), also deployed on the upper arm, for measuring orientation of the upper arm, as described in further detail hereinbelow.

The apparatus further includes a computer processor which derives control data from the measured pressure and orientation, and a transmitter which transmits the derived control data, over a wireless or wired connection, to the computing device.

The computer processor may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured pressures and orientations.

The control data as derived before transmission, may already comply with a standard computer mouse protocol, say the standard Microsoft™ serial mouse protocol that is supported by major operating systems, as known in the art.

Alternatively, the apparatus may further include a data converter (say a dedicated driver program) which runs on the computing device and converts the control data into control data that is compliant with a standard computer mouse protocol, or to other computer control data.

Consequently, the apparatus may translate movement of muscle of the upper arm, even after amputation, into computer control operations in general, and mouse functions in particular.

The apparatus may thus be suitable for use by amputees that hitherto have to rely on devices oriented towards paralyzed users and based on eye movement, brain waves or even air flow, etc., rather than operation of the muscle of the upper arm.

By employing operation of the muscle (say the triceps) of the upper arm (i.e. a stump), the present embodiment, may provide a more intuitive and non-invasive human-computer interface for amputees. The interface may provide a user experience closer to regular mouse operation than other alternatives currently available to arm amputees, as well as encourage continues use of the amputee's arm muscles.

The apparatus may also be used by non-amputees. For example, the apparatus may be used by workers who have to carry equipment or row materials in their hands, while interacting with a computing device (say a computer in an assembly line or in a warehouse).

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a block diagram schematically illustrating a first apparatus for upper-arm computer pointing, according to an exemplary embodiment of the present invention.

An exemplary apparatus 1000, according to an exemplary embodiment of the present invention, may be worn on an upper arm 101 of a user of a computing device, such as a desktop computer, a computer in an industrial environment, a smart cellular phone, etc., as known in the art.

For example, the apparatus 1000 may be worn on the upper arm 101, using a strap or a bracelet that parts of the apparatus 1000 may be fitted on.

The apparatus 1000 includes one or more sensors 110, say pressure meters (say Force Sensing Resistors), orientation measurers (say gyroscopic devices), etc., as described in further detail hereinbelow.

Optionally, the sensors 110 include one or more pairs of pressure meters that are arranged on the strap or bracelet, such that when the apparatus 1000 is worn by the user, each two pressure meters of a pair are deployed on preferable areas of the upper arm 101.

In one example, the pair of pressure meters is positioned over opposite sides of the muscle (say the triceps), say a first pressure meter 110 opposite a second pressure meter 110.

Optionally, the two pressure meters serve as control references for each other, as providers of complementary information, etc., as described in further detail hereinbelow.

Similarly, the sensors 110 may include one or more pairs of orientation measurers that are arranged on the strap or bracelet, such that when the apparatus 1000 is worn by the user, each two orientation measurers of a pair are deployed on preferable areas of the upper arm 101, say on areas positioned over opposite sides of the muscle (say the triceps).

In one example, the pair of orientation measurers is positioned over opposite sides of the muscle, say a first orientation measurer 110 opposite a second orientation measurer 110.

Optionally, the two orientation measurers may be serve as control references for each other, as providers of complementary information, etc., as described in further detail hereinbelow.

The apparatus 1000 further includes a computer processor 130, connected to the sensors 110, which is programmed to derive control data from the sensor's 110 measurements, as described in further detail hereinbelow.

The computer processor 130 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measurements.

The apparatus 1000 further includes a transmitter 140 connected to the computer processor 130.

The transmitter 140 transmits the derived control data, over a wireless (say Bluetooth®) or over a wired connection, to the computing device.

Optionally, the control data as derived before transmission, already complies with a standard computer mouse protocol, say with the standard Microsoft™ serial mouse protocol that is supported by major operating systems, as known in the art.

Alternatively, the apparatus 1000 may further include a data converter (not shown), such as a driver program which runs on the computing device. The data converter converts the control data into control data that is compliant with a standard computer mouse protocol or to other computer control data, and inputs the converted data as input to the computing device's operating system, as described in further detail hereinbelow.

Consequently, the apparatus 1000 may translate movement of muscle of the upper arm 101 into computer control operations in general, and mouse functions in particular.

The apparatus 1000 may thus be suitable for use by amputees that hitherto have to rely on devices oriented towards paralyzed users and based on eye movement, brain waves or even air flow, etc., rather than operation of the muscle of the upper arm 101.

The apparatus 1000 may also be used by non-amputees. For example, the apparatus may be used by workers who have to carry equipment or row materials in their hands, while interacting with a computing device (say a computer in an assembly line or in a warehouse).

The apparatus 1000 may also include a power source (not shown), say one or more batteries, as known in the art.

Figure 2:
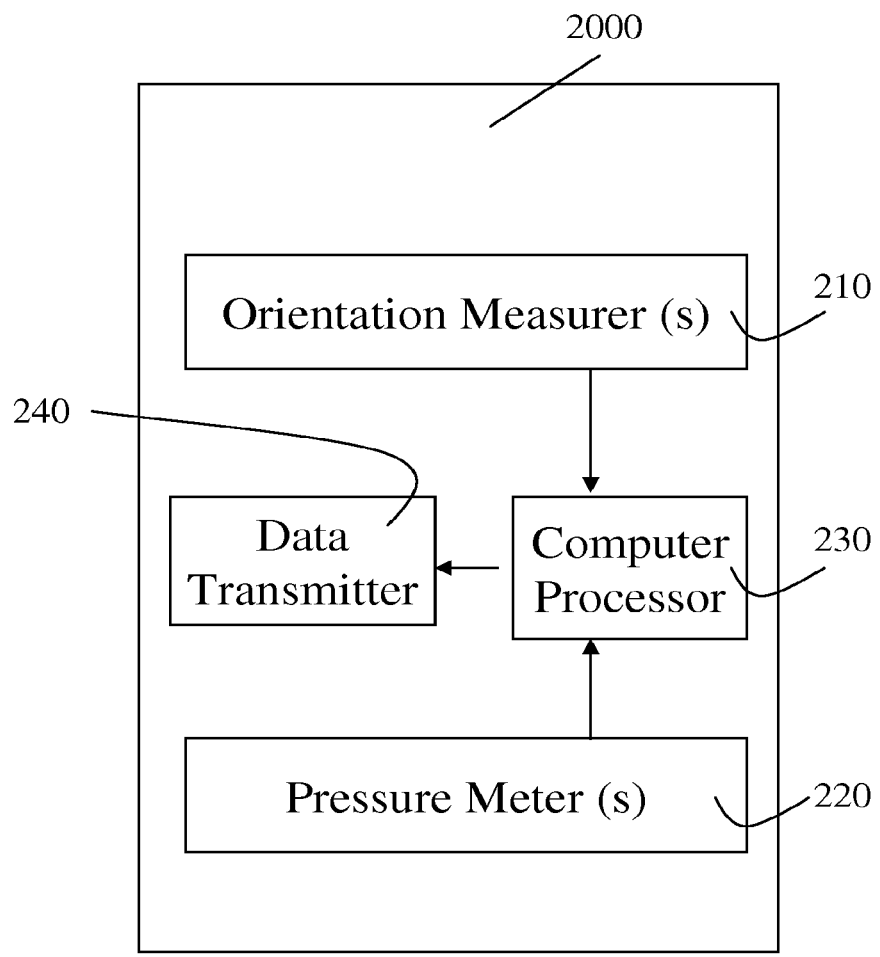
FIG. 2 is a block diagram schematically illustrating a second apparatus for upper-arm computer pointing, according to an exemplary embodiment of the present invention.

Reference is now made to FIG. 2, which is a block diagram schematically illustrating a second apparatus for upper-arm computer pointing, according to an exemplary embodiment of the present invention.

An exemplary apparatus 2000, according to an exemplary embodiment of the present invention, may be worn on an upper arm of a user of a computing device.

The computing device may include, but is not limited to: a desktop computer, a computer in an industrial environment, a smart cellular phone, etc, or any other computing device in use by the user of the apparatus 2000, as known in the art.

The apparatus 2000 includes one or more orientation measurers 210, deployable on one or more areas of an upper arm of a user, say using a strap or a bracelet wearable on the upper arm, on which the one or more orientation measurers 210 are arranged, as described in further detail hereinabove.

Each one of the orientation measurers 210 measures orientation of the upper arm, on the area on which the orientation measurer 210 is deployed.

Each one of the orientation measurers 210 may include, but is not limited to one or more of: a gyroscope, a GPS (Global Positioning System) receiver, an accelerometer, an IMU (Inertial Measurement Unit), etc., as known in the art, or any combination thereof.

Optionally, one or more of the orientation measurers 210 measures angular orientation of the upper arm.

For example, the orientation measurer 210 may measure an angle of inclination of the orientation measurer 210, and hence of the upper arm, with respect to a preselected surface of reference. The measured angle may also be described as a rotation that would be needed to move the orientation measurer 210 from the surface to the orientation measurer's 210 location, as known in the art.

Optionally, one or more of the orientation measurers 210 measures bi-dimensional positional orientation of the orientation measurer 210, and hence of the upper arm. For example, the orientation measurer 210 may measure position of the orientation measurer's 210 projection on a preselected surface of reference, as known in the art.

Optionally, one or more of the orientation measurers 210 measures tri-dimensional positional orientation of the orientation measurer 210, and hence of the upper arm. For example, the orientation measurer 210 may measure the orientation measurer's 210 spatial position, with respect to a pre-defined three dimensional coordinate system, as known in the art.

Optionally, the orientation measurers 210 include one or more pairs of orientation measurers 210 that are arranged on the strap or bracelet, such that when the apparatus 2000 is worn by the user, each two orientation measurers 210 of a pair are deployed on preferable areas of the user's upper arm.

In one example, the pair of orientation measurers 210 is positioned over opposite sides of the muscle (say the triceps), say a first orientation measurer 210 opposite a second orientation measurer 210.

Optionally, the two orientation measurers 210 of each pair serve as control references for each other, as providers of complementary information (i.e. measurement), etc., as described in further detail hereinbelow.

The apparatus 2000 further includes one or more pressure meters 220, deployable on one or more areas of an upper arm of a user.

Each of the pressure meters 220 measures pressure on the upper arm's area on which the pressure meter 220 is deployed.

Each one of the pressure meters 220 may include, but is not limited to one or more of: a conductive polymer based pressure sensor such as an FSR (Force Sensing Resistor), a capacitive-based pressure sensor, an electromagnetic sensor, etc., as known in the art, or any combination thereof.

Optionally, the pressure meters 220 include one or more pairs of pressure meters 220 that are arranged on the strap or bracelet, such that when the apparatus 2000 is worn by the user, each two pressure meters 220 of a pair are deployed on preferable areas of the user's upper arm.

In one example, the pair of pressure meters 220 is positioned over opposite sides of the muscle (say the triceps), say a first pressure meter 220 opposite a second pressure meter 220.

The two pressure meters 220 of each pair may serve as control references for each other, as providers of complementary information (i.e. measurements), etc., as described in further detail hereinbelow.

The apparatus 2000 further includes a computer processor 230, in communication with the orientation measurers 210 and pressure meters 220.

The computer processor 230 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured orientations and pressures.

The computer processor 230 is configured (say by programming), to derive control data from the measured orientation and pressure, as described in further detail hereinbelow.

Optionally, the computer processor 230 compares a measurement of a first one of the orientation measurers 210 with a measurement of a second one of the orientation measurers 210, for deriving the control data.

In one example, the computer processor 230 may use measurements of two orientation measurers 210 deployed on opposite sides of the upper arm's muscle, as control references of each other (say by verifying that the two measurements do not significantly differ from each other).

In a second example, the computer processor 230 may use measurements of two orientation measurers 210 deployed on opposite sides of the upper arm's muscle, as complementary information, for deriving the control data.

For example, the computer processor 230 may use calculations based on measurements by both orientation measurers 210 of the pair, for deriving the control data.

Optionally, the calculations are of a change in angular orientation of a theoretical line which connects the two orientation measurers 210, with respect to a preselected surface of reference.

Similarly, the computer processor 230 may compare a measurement of a first one of the pressure meters 220 with a measurement of a second one of the pressure meters 220, for deriving the control data.

In one example, the computer processor 230 may use measurements of two pressure meters 220 deployed on opposite sides of the upper arm's muscle, as control references of each other (say by verifying that the two measurements do not significantly differ from each other).

In a second example, the computer processor 230 may use measurements of two pressure meters 220 deployed on opposite sides of the upper arm's muscle, as complementary information, for deriving the control data.

For example, the computer processor 230 may use calculations based on measurements by both pressure meters 220 of the pair, for deriving the control data.

The apparatus 2000 further includes a data transmitter 240, in communication with the computer processor 230.

The transmitter 240 transmits the control data to the computing device in use by the user of apparatus 2000.

Optionally, the transmitter 240 transmits the control data to the computing device over a wired connection. For example, the transmitter 240 may include an electric circuit that transmits the control data over wires. The wires may be connected to one of the computing device's USB (Universal Serial Bus) sockets, to a communications socket of a communications card installed in the computing device, etc., as known in the art.

Optionally, the transmitter 240 transmits the control data to the computing device over a wireless connection. For example, the transmitter 240 may include an electronic communications circuit that transmits the control data as radio-frequency (RF) signals, say in the Bluetooth® frequency range (2.400 GHz-2.480 GHz).

Optionally, the computer processor 230 derives the control data as control data that is already compliant with a standard computer mouse protocol, say with the standard Microsoft™ serial mouse protocol (supported by major operating systems), as known in the art.

Optionally, the computer processor 230 does not derive the control data as compliant with a standard mouse protocol, but the apparatus 2000 further includes a data converter (not shown) implemented on the computing device, say a driver program which runs on the computing device.

The data converter receives the transmitted control data, converts the control data into control data that is compliant with the standard computer mouse protocol, and inputs the compliant control data to the computing device's operating system (say MS® Windows, Android, etc.).

Upon receipt of the control data compliant with the standard computer mouse protocol, the computing device's operating system reacts as if the control data originates from operations performed on a standard computer mouse.

Stated differently, the computer processor 230 may translate changes in pressure, orientation (or both), as measured by the pressure meters 220, orientation measurers 210 (or both), respectively, into computer mouse operation data. The computer mouse operation data causes the computing device to react as if the user uses a standard computer mouse rather than the apparatus 2000.

In one example, the computer processor 230 may translate a pressure change measured by one or more of the pressure meters 220, into computer mouse clicking operation data included in the derived control data.

Once the computing device's operating system receives the control data in a format compliant with a standard mouse protocol, the computing device reacts as if the control data originates from clicking a regular computer mouse (say a standard Microsoft® Mouse).

In a second example, the computer processor 230 may translate an angular orientation change measured by one or more of the orientation measurers 210, into computer mouse clicking operation data included in the derived control data. The control data may cause the computing device to reacts as if the control data originates from clicking a regular computer mouse (say a standard Microsoft® Mouse), as described in further detail hereinbelow.

In a third example, the computer processor 230 may translate a movement in a predefined direction, measured by one or more of the orientation measurers 210, into computer mouse clicking operation data included in the derived control data. The control data may cause the computing device to reacts as if the control data originates from clicking a regular computer mouse (say a standard Microsoft® Mouse), as described in further detail hereinbelow.

In a fourth example, the computer processor 230 may translate an angular orientation change measured by one or more of the orientation measurers 210, into mouse speed change data included in the derived control data (say data which brings about a change similar to a change in speed in which a user moves a computer mouse), as described in further detail hereinbelow.

Consequently, the apparatus 2000 may translate movement of muscle of the user's upper arm into computer control operations in general, and mouse functions in particular.

The apparatus 2000 may thus be suitable for use by amputees that hitherto have to rely on devices oriented towards paralyzed users and based on eye movement, brain waves or even air flow, etc., rather than operation of the muscle of the upper arm, as described in further detail hereinabove.

By employing operation of the muscle of the upper arm, the exemplary apparatus 2000 may provide a more intuitive and non-invasive human-computer interface for amputees, as well as encourage continues use of the amputee's arm muscles.

The apparatus 2000 may also be used by non-amputees. For example, the apparatus 2000 may be used by workers who have to carry equipment or row materials in their hands, while interacting with a computing device (say a computer in an assembly line or in a warehouse).

The apparatus 2000 may also include a power source (not shown), say one or more batteries, as known in the art.

Figure 3:
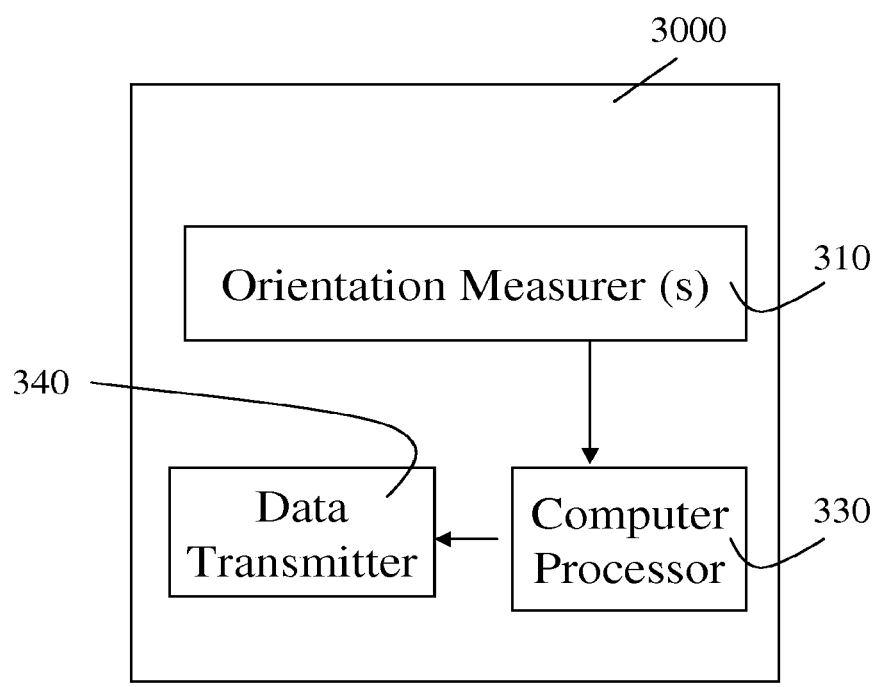
FIG. 3 is a block diagram schematically illustrating a third apparatus for upper-arm computer pointing, according to an exemplary embodiment of the present invention.

Reference is now made to FIG. 3, which is a block diagram schematically illustrating a third apparatus for upper-arm computer pointing, according to an exemplary embodiment of the present invention.

An exemplary apparatus 3000, according to an exemplary embodiment of the present invention, may be worn on an upper arm of a user of a computing device.

The computing device may include, but is not limited to: a desktop computer, a computer in an industrial environment, a smart cellular phone, etc, or any other computing device in use by the user of the apparatus 3000, as known in the art.

The apparatus 3000 includes one or more orientation measurers 310, deployable on one or more areas of an upper arm of a user, say using a strap or a bracelet wearable on the upper arm, on which the one or more orientation measurers 310 are arranged, as described in further detail hereinabove.

Each one of the orientation measurers 310 measures orientation of the upper arm, on the area on which the orientation measurer 310 is deployed.

Each one of the orientation measurers 310 may include, but is not limited to one or more of: a gyroscope, a GPS (Global Positioning System) receiver, an accelerometer, an IMU (Inertial Measurement Unit), etc., as known in the art, or any combination thereof.

Optionally, one or more of the orientation measurers 310 measures angular orientation of the upper arm.

For example, the orientation measurer 310 may measure an angle of inclination of the orientation measurer 310, and hence of the upper arm, with respect to a preselected surface of reference. The measured angle may also be described as a rotation that would be needed to move the orientation measurer 310 from the surface to the orientation measurer's 310 location, as known in the art.

Optionally, one or more of the orientation measurers 310 measures bi-dimensional positional orientation of the orientation measurer 310, and hence of the upper arm. For example, the orientation measurer 310 may measure position of the orientation measurer's 310 projection on a preselected surface of reference, as known in the art.

Optionally, one or more of the orientation measurers 230 measures tri-dimensional positional orientation of the orientation measurer 310, and hence of the upper arm. For example, the orientation measurer 310 may measure the orientation measurer's 310 spatial position, with respect to a pre-defined three dimensional coordinate system, as known in the art.

Optionally, the orientation measurers 310 include one or more pairs of orientation measurers 310 that are arranged on the strap or bracelet, such that when the apparatus 3000 is worn by the user, each two orientation measurers 310 of a pair are deployed on preferable areas of the user's upper arm.

In one example, the pair of orientation measurers 310 is positioned over opposite sides of the muscle (say the triceps), say a first orientation measurer 310 opposite a second orientation measurer 310.

Optionally, the two orientation measurers 310 of each pair serve as control references for each other, as providers of complementary information (i.e. measurement), etc., as described in further detail hereinbelow.

The apparatus 3000 further includes a computer processor 330, in communication with the orientation measurers 310.

The computer processor 330 is configured (say by programming), to derive control data from the orientation measured by the orientation measurers 310, as described in further detail hereinbelow.

The computer processor 330 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured orientations.

Optionally, the computer processor 330 compares a measurement of a first one of the orientation measurers 310 with a measurement of a second one of the orientation measurers 310, for deriving the control data.

In one example, the computer processor 330 may use measurements of two orientation measurers 310 deployed on opposite sides of the upper arm's muscle, as control references of each other (say by verifying that the two measurements do not significantly differ from each other).

In a second example, the computer processor 330 may use measurements of two orientation measurers 310 deployed on opposite sides of the upper arm's muscle (say triceps), as complementary information, for deriving the control data.

For example, the computer processor 330 may use calculations based on measurements by both orientation measurers 310 of the pair, for deriving the control data.

Optionally, the calculations are of a change in angular orientation of a theoretical line which connects the two orientation measurers 310, with respect to a preselected surface of reference.

The apparatus 3000 further includes a data transmitter 340, in communication with the computer processor 330.

The transmitter 340 transmits the control data to the computing device in use by the user of apparatus 3000.

Optionally, the transmitter 340 transmits the control data to the computing device over a wired connection. For example, the transmitter 240 may include an electric circuit that transmits the control data over wires connected to one of the computing device's USB (Universal Serial Bus) sockets, etc., as known in the art.

Optionally, the transmitter 340 transmits the control data to the computing device over a wireless connection. For example, the transmitter 340 may include an electronic communications circuit that transmits the control data as radio-frequency (RF) signals, say in the Bluetooth® frequency range.

Optionally, the computer processor 330 derives the control data as control data that is already compliant with a standard computer mouse protocol, say with the standard Microsoft™ serial mouse protocol (supported by major operating systems), as known in the art.

Optionally, the computer processor 330 does not derive the control data as compliant with a standard mouse protocol, but the apparatus 3000 further includes a data converter (not shown) implemented on the computing device, say a driver program which runs on the computing device.

The data converter receives the transmitted control data, converts the control data into control data that is compliant with the standard computer mouse protocol, and inputs the compliant control data to the computing device's operating system (say MS® Windows, Android, etc.).

Upon receipt of the control data compliant with the standard computer mouse protocol, the computing device's operating system reacts as if the control data originates from operations performed on a standard computer mouse.

That is to say the computer processor 330 may translate changes in orientation, as measured by the orientation measurers 310, into computer mouse operation data. The computer mouse operation data causes the computing device to react as if the user uses a standard computer mouse rather than the apparatus 3000.

In one example, the computer processor 330 may translate an angular orientation change measured by one or more of the orientation measurers 310, into computer mouse clicking operation data included in the derived control data.

Once the computing device's operating system receives the control data in a format compliant with a standard mouse protocol, the computing device reacts as if the control data originates from clicking a regular computer mouse (say a standard Microsoft® Mouse).

In a second example, the computer processor 330 may translate a movement in a predefined direction, measured by one or more of the orientation measurers 310, into computer mouse clicking operation data included in the derived control data. The control data may cause the computing device to reacts as if the control data originates from clicking a regular computer mouse (say a standard Microsoft® Mouse), as described in further detail hereinbelow.

In a third example, the computer processor 330 may translate an angular orientation change measured by one or more of the orientation measurers 310, into mouse speed change data included in the derived control data (say data which brings about a change similar to a change in speed in which a user moves a computer mouse).

Consequently, the apparatus 3000 may translate movement of muscle of the user's upper arm into computer control operations in general, and mouse functions in particular.

The apparatus 3000 may thus be suitable for use by amputees that hitherto have to rely on devices oriented towards paralyzed users and based on eye movement, brain waves or even air flow, etc., rather than operation of the muscle of the upper arm, as described in further detail hereinabove.

The apparatus 3000 may also be used by non-amputees. For example, the apparatus 3000 may be used by workers who have to carry equipment or row materials in their hands, while interacting with a computing device (say a computer in an assembly line or in a warehouse).

The apparatus 3000 may also include a power source (not shown), say one or more batteries, as known in the art.

Figure 4:
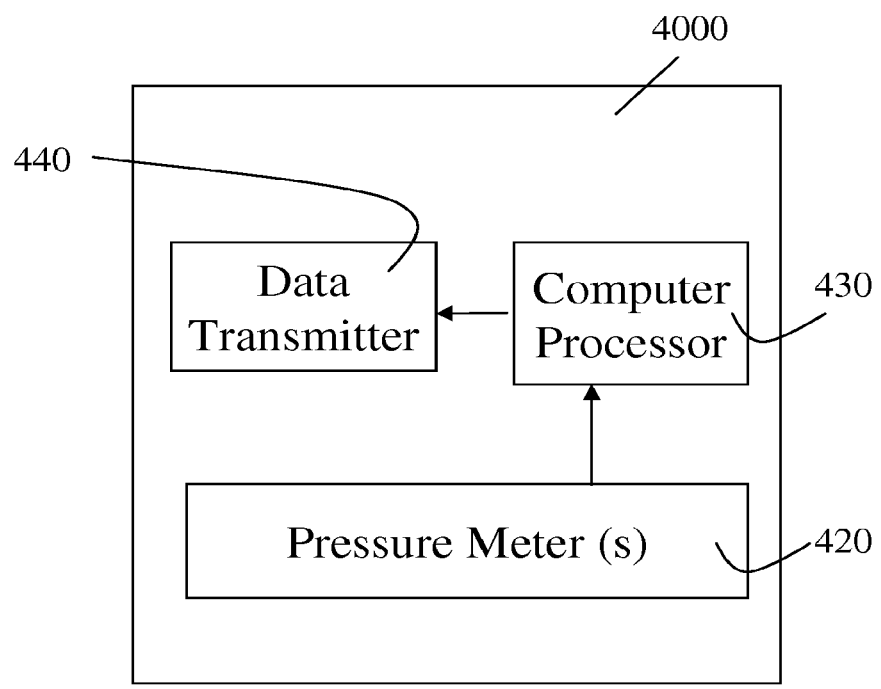
FIG. 4 is a block diagram schematically illustrating a fourth apparatus for upper-arm computer pointing, according to an exemplary embodiment of the present invention.

Reference is now made to FIG. 4, which is a block diagram schematically illustrating a fourth apparatus for upper-arm computer pointing, according to an exemplary embodiment of the present invention.

An exemplary apparatus 4000, according to an exemplary embodiment of the present invention, may be worn on an upper arm of a user of a computing device, as described in further detail hereinabove.

The computing device may include, but is not limited to: a desktop computer, a computer in an industrial environment, a smart cellular phone, etc, or any other computing device in use by the user of the apparatus 4000, as known in the art.

The apparatus 4000 includes one or more pressure meters 420, deployable on one or more areas of an upper arm of a user.

Each of the pressure meters 420 measures pressure on the upper arm's area on which the pressure meter 420 is deployed.

Each one of the pressure meters 420 may include, but is not limited to one or more of: a conductive polymer based pressure sensor such as an FSR (Force Sensing Resistor), a capacitive-based pressure sensor, an electromagnetic sensor, etc., as known in the art, or any combination thereof.

Optionally, the pressure meters 420 include one or more pairs of pressure meters 420 that are arranged on the strap or bracelet, such that when the apparatus 4000 is worn by the user, each two pressure meters 420 of a pair are deployed on preferable areas of the user's upper arm.

In one example, the pair of pressure meters 420 is positioned over opposite sides of the muscle (say the triceps), say a first pressure meter 420 opposite a second pressure meter 420.

The two pressure meters 420 of each pair may serve as control references for each other, as providers of complementary information (i.e. measurements), etc., as described in further detail hereinbelow.

The apparatus 4000 further includes a computer processor 430, in communication with the pressure meters 420.

The computer processor 430 is configured (say by programming), to derive control data from the measured pressure, as described in further detail hereinbelow.

The computer processor 430 may include, but is not limited to: a microprocessor, a microcontroller (typically having a processing unit as well as a fixed amount of RAM, ROM and other peripherals, embedded on a single chip), or any other hardware component (say an integrated circuit) capable on performing calculations based on the measured pressures.

The computer processor 430 may compare a measurement of a first one of the pressure meters 420 with a measurement of a second one of the pressure meters 420, for deriving the control data.

In one example, the computer processor 430 may use measurements of two pressure meters 420 deployed on opposite sides of the upper arm's muscle, as control references of each other (say by verifying that the two measurements do not significantly differ from each other).

In a second example, the computer processor 430 may use measurements of two pressure meters 420 deployed on opposite sides of the upper arm's muscle, as complementary information, for deriving the control data.

For example, the computer processor 430 may use calculations based on measurements by both pressure meters 420 of the pair, for deriving the control data.

The apparatus 4000 further includes a data transmitter 440, in communication with the computer processor 430.

The transmitter 440 transmits the control data to the computing device in use by the user of apparatus 4000.

Optionally, the transmitter 440 transmits the control data to the computing device over a wired connection. For example, the transmitter 240 may include an electric circuit that transmits the control data over wires. The wires may be connected to one of the computing device's USB (Universal Serial Bus) sockets, to a communications socket of a communications card installed in the computing device, etc., as known in the art.

Optionally, the transmitter 440 transmits the control data to the computing device over a wireless connection. For example, the transmitter 440 may include an electronic communications circuit that transmits the control data as radio-frequency (RF) signals, say in the Bluetooth® frequency range.

Optionally, the computer processor 430 derives the control data as control data that is already compliant with a standard computer mouse protocol, say with the standard Microsoft™ serial mouse protocol (supported by major operating systems), as known in the art.

Optionally, the computer processor 430 does not derive the control data as compliant with a standard mouse protocol, but the apparatus 4000 further includes a data converter (not shown) implemented on the computing device, say a driver program which runs on the computing device.

The data converter receives the transmitted control data, converts the control data into control data that is compliant with the standard computer mouse protocol, and inputs the compliant control data to the computing device's operating system (say MS® Windows, Android, etc.).

Upon receipt of the control data compliant with the standard computer mouse protocol, the computing device's operating system reacts as if the control data originates from operations performed on a standard computer mouse.

Stated differently, the computer processor 430 may translate changes in pressure, as measured by the pressure meters 420, into computer mouse operation data. The computer mouse operation data causes the computing device to react as if the user uses a standard computer mouse rather than the apparatus 4000.

For example, the computer processor 430 may translate a pressure change measured by one or more of the pressure meters 420 into computer mouse clicking operation data included in the derived control data.

Once the computing device's operating system receives the control data in a format compliant with a standard mouse protocol, the computing device reacts as if the control data originates from clicking a regular computer mouse (say a standard Microsoft® Mouse).

Consequently, the apparatus 4000 may translate movement of muscle of the user's upper arm into computer control operations in general, and mouse functions in particular.

The apparatus 4000 may thus be suitable for use by amputees that hitherto have to rely on devices oriented towards paralyzed users and based on eye movement, brain waves or even air flow, etc., rather than operation of the muscle of the upper arm, as described in further detail hereinabove.

The apparatus 4000 may also be used by non-amputees, say workers who have to carry equipment or row materials in their hands, while interacting with a computing device (say a computer in an assembly line or in a warehouse).

The apparatus 4000 may also include a power source (not shown), say one or more batteries, as known in the art.

Figure 5:
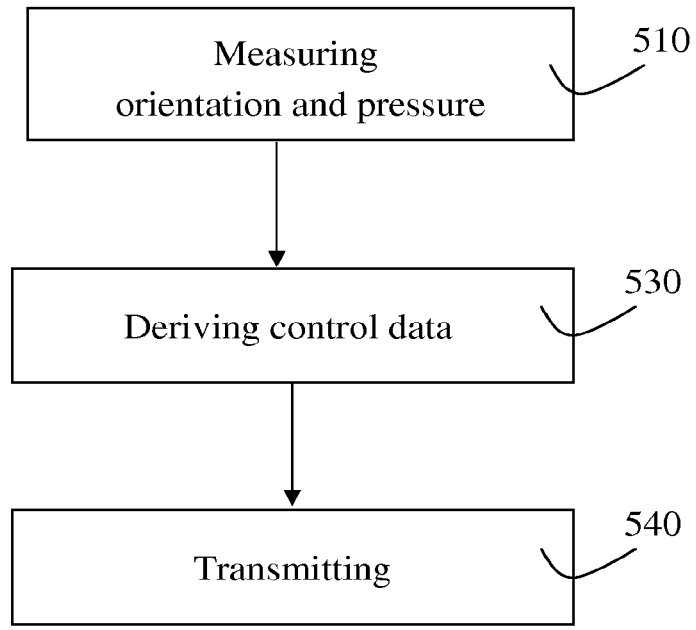
FIG. 5 is a flowchart illustrating a first method for upper-arm computer pointing, according to an exemplary embodiment of the present invention.

Reference is now made to FIG. 5, which is a flowchart illustrating a first method for upper-arm computer pointing, according to an exemplary embodiment of the present invention.

In a first exemplary method, according to an exemplary embodiment of the present invention, a computing device may be controlled by muscle of an upper arm of a user of the computing device, say through upper arm movement or pressure applied by the muscle on sides of the upper arm, as described in further detail hereinabove.

The computing device may include, but is not limited to: a desktop computer, a computer in an industrial environment, a smart cellular phone, etc, or any other computing device in use by the user.

In the exemplary method, orientation of the upper arm of the user is measured 510 on one or more areas of the upper arm, say by the orientation measurers 210 of apparatus 2000. Each one of the orientation measurers 210 measures orientation of the upper arm, on the area on which the orientation measurer 210 is deployed.

The orientation may be measured 510 using one or more of: a gyroscope, a GPS (Global Positioning System) receiver, an accelerometer, an IMU (Inertial Measurement Unit), etc., as known in the art, or any combination thereof.

Optionally, the measured 510 orientation is an angular orientation of the upper arm.

For example, the angular orientation may be measured 510 as an angle of inclination of the upper arm, with respect to a preselected surface of reference. The measured 510 angle may also be described as a rotation that would be needed to move the upper arm from the surface of reference, to the upper arm's location, as described in further detail hereinabove.

Optionally, the measured 510 orientation is a bi-dimensional positional orientation of the upper arm.

For example, the orientation may be measured 510 as position of the orientation measurer's 210 projection on a preselected surface of reference, as described in further detail hereinabove.

Optionally, the measured 510 orientation is a tri-dimensional positional orientation of the upper arm.

For example, the orientation may be measured 510 as the orientation measurer's 210 spatial position, with respect to a pre-defined three dimensional coordinate system, as described in further detail hereinabove.

The exemplary method further includes measuring 510 of pressure applied by muscle of the upper arm on one or more areas of the upper arm, say by the pressure meters 220 of apparatus 2000 (where each pressure meter 220 is deployed on a respective one of the areas), as described in further detail hereinabove.

The method further includes deriving 530 control data from the measured 510 pressure and orientation, say by the computer processor 230 of apparatus 2000, as described in further detail hereinabove.

Optionally, the method further includes comparing an orientation measured 510 on a first area of the upper arm with an orientation measured 510 on a second area of the upper arm, for deriving the control data. The orientations may be measured 510 by a pair of orientation measurers 210 deployed on opposite sides of the upper arm's muscle, as described in further detail hereinabove.

In one example, a pair of orientations measured 510 on opposite sides of the upper arm's muscle (say the triceps), may be used as control references of each other (say by verifying that the two measured 510 orientations do not significantly differ from each other), as described in further detail hereinabove.

In a second example, a pair of orientations measured 510 on opposite sides of the upper arm's muscle, may be used as complementary information, for deriving the control data.

For example, calculations based on orientations measured 510 by both orientation measurers 210 of a pair of orientation measurers 210 deployed over opposite sides of the upper arm muscle, may be used for deriving the control data.

Optionally, the calculations are of a change in angular orientation of a theoretical line which connects the two orientation measurers 210 of the pair, with respect to a preselected surface of reference, as described in further detail hereinabove.

Similarly, the method may include comparing pressures measured 510 on at least two of the upper arm areas, for deriving the control data, say using a pair of pressure meters 220 deployed on opposite sides of the upper arm's muscle, opposite each other, as described in further detail hereinabove.

In one example, pressures measured 510 on at least two of the areas are used as control references of each other (say by verifying that the two measured 510 pressures do not significantly differ from each other).

In a second example, pressures measured 510 on at least two of the areas, are used as complementary information, for deriving the control data, say through calculations based on pressures measured 510 by both pressure meters 220 of a pair, as described in further detail hereinabove.

Then, the derived 530 control data is transmitted 540 to the computing device, say using the transmitter 240 of apparatus 2000.

Optionally, the derived 530 control data is transmitted 540 over a wired connection, say over wires connected to one of the computing device's USB (Universal Serial Bus) sockets, to a communications socket of a communications card installed in the computing device, etc., as known in the art.

Optionally, the derived 530 control data is transmitted 540 over a wireless connection, say as radio-frequency (RF) signals in the Bluetooth® frequency range (2.400 GHz-2.480 GHz) or in another frequency range.

Optionally, the control data is derived 530 as control data that is already compliant with a standard computer mouse protocol, say with the standard Microsoft™ serial mouse protocol (supported by major operating systems), as known in the art.

Optionally, the derived 530 control data does not comply with a standard mouse protocol, but upon receipt on the computing device, is converted into control data that is compliant with the standard computer mouse protocol, on the computing device, say by the data converter of apparatus 2000.

The compliant control data is input to the computing device's operating system (say MS® Windows, Android, etc.), say by the data converter of apparatus 2000.

Upon receipt of the control data compliant with the standard computer mouse protocol, the computing device's operating system reacts as if the control data originates from operations performed on a standard computer mouse.

Stated differently, in the exemplary method, changes in pressure, orientation, or both, as measured 510 on the areas of the upper arm, are translated into computer mouse operation data. The computer mouse operation data causes the computing device to react as if the user uses a standard computer mouse.

In one example, a pressure change measured 510 on one or more areas of the upper arm, is translated into computer mouse clicking operation data included in the derived 530 control data.

Once the computing device's operating system receives the control data in a format compliant with a standard mouse protocol, the computing device reacts as if the control data originates from clicking a regular computer mouse (say a standard Microsoft® Mouse).

In a second example, an angular orientation change measured 510 on one or more areas of the upper arm, is translated into computer mouse clicking operation data included in the derived 530 control data.

Consequently, the control data may cause the computing device to reacts as if the control data originates from clicking a regular computer mouse (say a standard Microsoft® Mouse), as described in further detail hereinabove.

In a third example, a movement in a predefined direction, measured 510 on one or more areas of the upper arm, is translated into computer mouse clicking operation data included in the derived 530 control data.

Consequently, the control data may cause the computing device to reacts as if the control data originates from clicking a regular computer mouse (say a standard Microsoft® Mouse), as described in further detail hereinabove.

In a fourth example, an angular orientation change measured 510 on one or more areas of the upper arm, is translated into mouse speed change data included in the derived 530 control data (say data which brings about a change similar to a change in speed in which a user moves a computer mouse).

The method may thus be suitable for amputees that hitherto have to rely on devices oriented towards paralyzed users and based on eye movement, brain waves or even air flow, etc., rather than operation of the muscle of the upper arm, as described in further detail hereinabove.

The method is usable for non-amputees too. For example, for workers who have to carry equipment or row materials in their hands, while interacting with a computing device (say a computer in an assembly line or in a warehouse), as described in further detail hereinabove.

Figure 6:
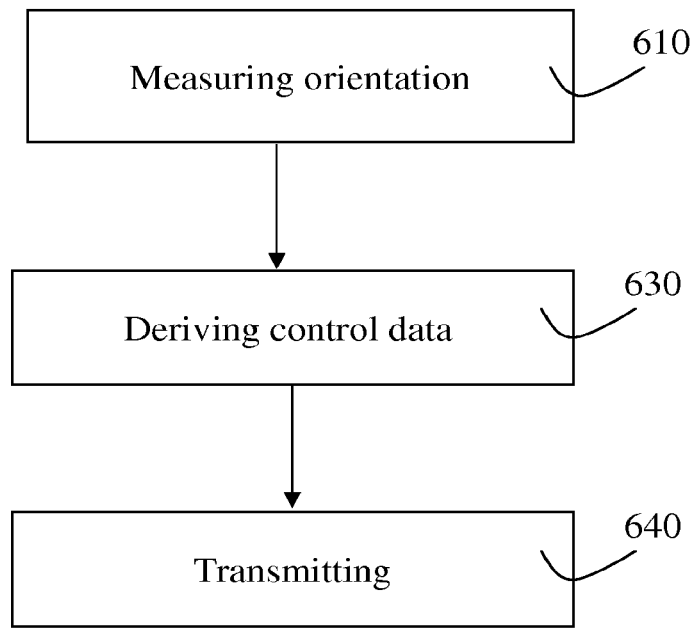
FIG. 6 is a flowchart illustrating a second method for upper-arm computer pointing, according to an exemplary embodiment of the present invention.

Reference is now made to FIG. 6, which is a flowchart illustrating a second method for upper-arm computer pointing, according to an exemplary embodiment of the present invention.

In a second exemplary method, according to an exemplary embodiment of the present invention, a computing device may be controlled by muscle of an upper arm of a user of a computing device, say by movement of the upper arm, as described in further detail hereinabove.

The computing device may include, but is not limited to: a desktop computer, a computer in an industrial environment, a smart cellular phone, etc, or any other computing device in use by the user.

In the exemplary method, orientation of the upper arm of the user is measured 610 on one or more areas of the upper arm, say by the orientation measurers 310 of apparatus 3000. Each one of the orientation measurers 310 measures orientation of the upper arm, on the area on which the orientation measurer 310 is deployed.

The orientation may be measured 610 using one or more of: a gyroscope, a GPS (Global Positioning System) receiver, an accelerometer, an IMU (Inertial Measurement Unit), etc., as known in the art, or any combination thereof.

Optionally, the measured 610 orientation is an angular orientation of the upper arm.

For example, the angular orientation may be measured 610 as an angle of inclination of the upper arm, with respect to a preselected surface of reference. The measured 610 angle may also be described as a rotation that would be needed to move the upper arm from the surface of reference, to the upper arm's location, as described in further detail hereinabove.

Optionally, the measured 610 orientation is a bi-dimensional positional orientation of the upper arm.

For example, the orientation may be measured 610 as position of the orientation measurer's 310 projection on a preselected surface of reference, as described in further detail hereinabove.

Optionally, the measured 610 orientation is a tri-dimensional positional orientation of the upper arm.

For example, the orientation may be measured 610 as the orientation measurer's 310 spatial position, with respect to a pre-defined three dimensional coordinate system, as described in further detail hereinabove.

The method further includes deriving 630 control data from the measured 610 orientation, say by the computer processor 330 of apparatus 3000, as described in further detail hereinabove.

Optionally, the method further includes comparing an orientation measured 610 on a first area of the upper arm with an orientation measured 610 on a second area of the upper arm, for deriving the control data. The orientations may be measured 610 by a pair of orientation measurers 310 deployed opposite each other, say on opposite sides of the upper arm's muscle, as described in further detail hereinabove.

In one example, a pair of orientations measured 610 on opposite sides of the upper arm's muscle (say the triceps), may be used as control references of each other (say by verifying that the two measured 610 orientations do not significantly differ from each other), as described in further detail hereinabove.

In a second example, a pair of orientations measured 610 on opposite sides of the upper arm's muscle, may be used as complementary information, for deriving the control data.

For example, calculations based on orientations measured 610 by both orientation measurers 310 of a pair of orientation measurers 310 deployed over opposite sides of the upper arm muscle, may be used for deriving the control data.

Optionally, the calculations are of a change in angular orientation of a theoretical line which connects the two orientation measurers 310 of the pair, with respect to a preselected surface of reference, as described in further detail hereinabove.

Then, the derived 630 control data is transmitted 640 to the computing device, say using the transmitter 340 of apparatus 3000.

Optionally, the derived 630 control data is transmitted 640 over a wired connection, say over wires connected to one of the computing device's USB (Universal Serial Bus) sockets, to a communications socket of a communications card installed in the computing device, etc., as known in the art.

Optionally, the derived 630 control data is transmitted 640 over a wireless connection, say as radio-frequency (RF) signals in the Bluetooth® frequency range (2.400 GHz-2.480 GHz) or in another frequency range.

Optionally, the control data is derived 630 as control data that is already compliant with a standard computer mouse protocol, say with the standard Microsoft™ serial mouse protocol (supported by major operating systems), as known in the art.

Optionally, the derived 630 control data does not comply with a standard mouse protocol, but upon receipt on the computing device, is converted into control data that is compliant with the standard computer mouse protocol, on the computing device, say by the data converter of apparatus 3000.

The compliant control data is input to the computing device's operating system (say MS® Windows, Android, etc.), say by the data converter of apparatus 3000.

Upon receipt of the control data compliant with the standard computer mouse protocol, the computing device's operating system reacts as if the control data originates from operations performed on a standard computer mouse.

Stated differently, in the exemplary method, changes in orientation of the upper arm of the user, as measured 610 on the areas of the upper arm, are translated into computer mouse operation data. The computer mouse operation data causes the computing device to react as if the user uses a standard computer mouse.

In one example, an angular orientation change measured 610 on one or more areas of the upper arm, is translated into computer mouse clicking operation data included in the derived 630 control data.

Once the computing device's operating system receives the control data in a format compliant with a standard mouse protocol, the computing device reacts as if the control data originates from clicking a regular computer mouse (say a standard Microsoft® Mouse).

In a second example, a movement in a predefined direction, measured 610 on one or more areas of the upper arm, is translated into computer mouse clicking operation data included in the derived 630 control data.

Consequently, the control data may cause the computing device to reacts as if the control data originates from clicking a regular computer mouse (say a standard Microsoft® Mouse), as described in further detail hereinabove.

In a third example, an angular orientation change measured 610 on one or more areas of the upper arm, is translated into mouse speed change data included in the derived 630 control data (say data which brings about a change similar to a change in speed in which a user moves a computer mouse).

The method may thus be suitable for amputees that hitherto have to rely on devices oriented towards paralyzed users and based on eye movement, brain waves or even air flow, etc., rather than operation of the muscle of the upper arm, as described in further detail hereinabove.

The method is usable for non-amputees too. For example, for workers who have to carry equipment or row materials in their hands, while interacting with a computing device (say a computer in an assembly line or in a warehouse), as described in further detail hereinabove.

Figure 7:
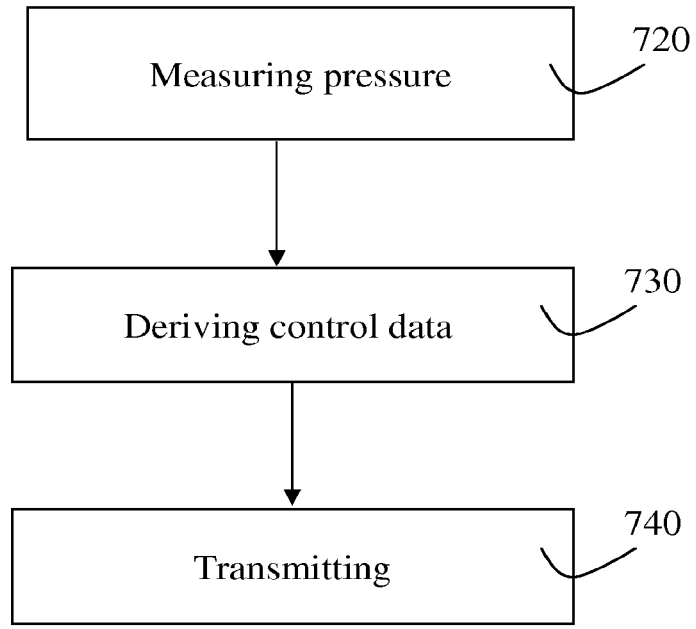
FIG. 7 is a flowchart illustrating a third method for upper-arm computer pointing, according to an exemplary embodiment of the present invention.

Reference is now made to FIG. 7, which is a flowchart illustrating a third method for upper-arm computer pointing, according to an exemplary embodiment of the present invention.

In a third exemplary method, according to an exemplary embodiment of the present invention, a computing device may be controlled by muscle of an upper arm of a user of a computing device, say through pressure applied by the muscle on sides of the upper arm, as described in further detail hereinabove.

The computing device may include, but is not limited to: a desktop computer, a computer in an industrial environment, a smart cellular phone, etc, or any other computing device in use by the user.

In the exemplary method, pressure applied by muscle of the upper arm on one or more areas of the upper arm is measured 720, say by the pressure meters 420 of apparatus 4000 (where each pressure meter 420 is deployed on a respective one of the areas), as described in further detail hereinabove.

The method further includes deriving 730 control data from the measured 720 pressure, say by the computer processor 430 of apparatus 4000, as described in further detail hereinabove.

Optionally, the method includes comparing pressures measured 720 on at least two of the upper arm areas, for deriving the control data, say using a pair of pressure meters 420 deployed on opposite sides of the upper arm's muscle, opposite each other, as described in further detail hereinabove.

In one example, pressures measured 720 on at least two of the areas are used as control references of each other (say by verifying that the two measured 720 pressures do not significantly differ from each other).

In a second example, pressures measured 720 on at least two of the areas, are used as complementary information, for deriving the control data, say through calculations based on pressures measured 720 by both pressure meters 420 of a pair, as described in further detail hereinabove.

Then, the derived 730 control data is transmitted 740 to the computing device, say using the transmitter 440 of apparatus 4000.

Optionally, the derived 730 control data is transmitted 740 over a wired connection, say over wires connected to one of the computing device's USB (Universal Serial Bus) sockets, to a communications socket of a communications card installed in the computing device, etc., as known in the art.

Optionally, the derived 730 control data is transmitted 740 over a wireless connection, say as radio-frequency (RF) signals in the Bluetooth® frequency range (2.400 GHz-2.480 GHz) or in another frequency range.

Optionally, the control data is derived 730 as control data that is already compliant with a standard computer mouse protocol, say with the standard Microsoft™ serial mouse protocol (supported by major operating systems), as known in the art.

Optionally, the derived 730 control data does not comply with a standard mouse protocol, but upon receipt on the computing device, is converted into control data that is compliant with the standard computer mouse protocol, on the computing device, say by the data converter of apparatus 4000.

The compliant control data is input to the computing device's operating system (say MS® Windows, Android, etc.), say by the data converter of apparatus 4000.

Upon receipt of the control data compliant with the standard computer mouse protocol, the computing device's operating system reacts as if the control data originates from operations performed on a standard computer mouse.

Stated differently, in the exemplary method, changes in pressure applied to one or more areas of the upper arm, as measured 720 on the areas of the upper arm, are translated into computer mouse operation data. The computer mouse operation data causes the computing device to react as if the user uses a standard computer mouse.

For example, a pressure change measured 720 on one or more areas of the upper arm, may be translated into computer mouse clicking operation data included in the derived 730 control data.

Once the computing device's operating system receives the control data in a format compliant with a standard mouse protocol, the computing device reacts as if the control data originates from clicking a regular computer mouse (say a standard Microsoft® Mouse).

The method may thus be suitable for amputees that hitherto have to rely on devices oriented towards paralyzed users and based on eye movement, brain waves or even air flow, etc., rather than operation of the muscle of the upper arm, as described in further detail hereinabove.

The method is usable for non-amputees too. For example, for workers who have to carry equipment or row materials in their hands, while interacting with a computing device (say a computer in an assembly line or in a warehouse), as described in further detail hereinabove.

It is expected that during the life of this patent many relevant devices and systems will be developed and the scope of the terms herein, particularly of the terms "Computer", "Computing Device", "Computer Processor", "Electric Circuit", "Wires", "Communications Card", "Operating System", "Radio Frequency (RF) Signals", "USB (Universal Serial Bus)", "Smart Cellular Phone", "Gyroscope", "GPS (Global Positioning System)", "IMU (Inertial Measurement Unit)", "Conductive Polymer", "Pressure Sensor", "FSR (Force Sensing Resistor)", "Capacitive-based Pressure Sensor", "Electromagnetic Pressure Sensor" and "Computer Mouse", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A wearable computer pointing apparatus, comprising:
a wearable apparatus adapted for placement about a body portion of a user comprising:
at least one orientation measurer, deployable over muscle of the body portion of the user, configured to electromechanically measure orientation of the body portion;
a computer processor physically attached to the wearable apparatus, associated with the orientation measurer, configured to (i) derive control data from the measured orientation and (ii) translate at least one of an angular orientation change or a movement in a predefined direction measured by the orientation measurer into input data included in the control data; and
a data transmitter physically attached to the wearable apparatus, associated with the computer processor, configured to transmit the control data to a computing device in communication with the wearable computer pointing apparatus, wherein:
the computing device is different than the computer processor, located physically apart from the wearable apparatus and externally connected to the wearable computer pointing apparatus;
the wearable computer pointing apparatus is configured to control an operation of the computing device based on the control data, thereby allowing the user to remotely control the computing device; and
the input data is configured to provide a selection operation at the computing device.

2. The wearable computer pointing apparatus of claim 1, wherein the data transmitter is further configured to transmit the control data to the computing device over a wireless connection.

3. The wearable computer pointing apparatus of claim 1, further comprising a data convertor, implemented on the computing device, configured to receive the transmitted control data and convert the transmitted control data into mouse protocol compliant control data.

4. The wearable computer pointing apparatus of claim 1, wherein the computer processor is further configured to derive the control data as mouse protocol compliant control data.

5. The wearable computer pointing apparatus of claim 1, wherein the at least one orientation measurer comprises at least two orientation measurers deployable on the body portion, and the computer processor is further configured to compare a measurement of a first one of the orientation measurers with a measurement of a second one of the orientation measurers, for deriving the control data.

6. The wearable computer pointing apparatus of claim 1, wherein at least one of the at least one orientation measurer comprises a GPS (Global Positioning System) receiver.

7. The wearable computer pointing apparatus of claim 1, wherein at least one of the at least one orientation measurer comprises an IMU (Inertial Measurement Unit).

8. The wearable computer pointing apparatus of claim 1, where the computer processor is further configured to translate an angular orientation change measured by at least one of the at least one orientation measurer into mouse speed change data included in the derived control data.

9. The wearable computer pointing apparatus of claim 1, wherein at least one of the at least one orientation measurer is further configured to measure angular orientation of the body portion.

10. The wearable computer pointing apparatus of claim 1, wherein at least one of the at least one orientation measurer is further configured to measure bi-dimensional positional orientation of the body portion.

11. The wearable computer pointing apparatus of claim 1, wherein at least one of the at least one orientation measurer is further configured to measure tri-dimensional positional orientation of the body portion.

12. The wearable computer pointing apparatus of claim 1, wherein the at least one orientation measurer is deployable over the muscle of the body portion of the user.

13. The wearable computer pointing apparatus of claim 1, wherein the at least one orientation measurer is further configured to electromechanically measure an angle of inclination of the body portion with respect to a preselected surface of reference.

14. The wearable computer pointing apparatus of claim 1, further comprising at least one pressure meter, deployable on at least one area of the body portion of the user, in communication with the computer processor, configured to measure pressure applied by the muscle of the body portion, wherein the computer processor is configured to derive the control data from the measured orientation and the measured pressure.

15. The wearable computer pointing apparatus of claim 14, wherein the at least one pressure meter comprises at least two pressure meters deployable on the body portion, over opposite sides of the muscle, and the computer processor is further configured to compare a first measurement of a first one of the pressure meters with a second measurement of a second one of the pressure meters, for deriving the control data and to identify a tremor of the muscle based on the comparison and a deviation of the first measurement from a reference value over time.

16. The wearable computer pointing apparatus of claim 14, wherein at least one of the at least one pressure meter comprises an FSR (Force Sensing Resistor).

17. The wearable computer pointing apparatus of claim 14, wherein the computer processor is further configured to translate a pressure change measured by at least one of the at least one pressure meter into the input data included in the derived control data.

18. A wearable computer pointing apparatus, comprising:
a wearable apparatus adapted for placement about a body portion an upper arm of a user comprising:
at least one pressure meter, deployable over muscle of the body portion of the user, configured to measure pressure applied by the muscle of the body portion;
a computer processor physically attached to the wearable apparatus, associated with the pressure meter, configured to (i) derive control data from the measured pressure and (ii) translate a pressure change measured by the pressure meter into input data included in the control data; and a data transmitter physically attached to the wearable apparatus, associated with the computer processor, configured to transmit the control data to a computing device in communication with the wearable computer pointing apparatus, wherein:

the computing device is different than the computer processor, located physically apart from the wearable apparatus and externally connected to the wearable computer pointing apparatus;

the wearable computer pointing apparatus is configured to control an operation of the computing device based on the control data, thereby allowing the user to remotely control the computing device; and the input data is configured to provide a selection operation at the computing device.

19. A method for computer pointing, comprising:

positioning an apparatus over muscle of a body portion an of a user;

electromechanically measuring orientation of the body portion of the user, on at least one area of the body portion using the apparatus that comprises an accelerometer, a gyroscope, or both an accelerometer and a gyroscope;

deriving control data from the measured orientation;

translating at least one of an angular orientation change or a movement in a predefined direction measured by the apparatus into input data included in the control data;

transmitting the control data to a computing device in communication with the apparatus, wherein the input data is configured to provide a selection operation at the computing device; and controlling an operation of the computing device based on the control data, thereby allowing the user to remotely control the computing device.

20. A method for computer pointing, comprising:

using an apparatus that comprises at least one pressure meter deployed over muscle of a body portion an of a user, measuring pressure applied by the muscle of the body portion on the pressure meter;

deriving control data from the measured pressure;

translating a pressure change measured by the apparatus into input data included in the control data;

transmitting the control data to a computing device in communication with the apparatus, wherein the input data is configured to provide a selection operation at the computing device; and controlling an operation of the computing device based on the control data, thereby allowing the user to remotely control the computing device.

\* \* \* \* \*